(12) United States Patent
Colacot

(10) Patent No.: US 8,754,250 B2
(45) Date of Patent: Jun. 17, 2014

(54) PROCESS FOR THE PREPARATION OF A PALLADIUM COMPLEX

(75) Inventor: Thomas John Colacot, Cherry Hill, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 13/579,504

(22) PCT Filed: Feb. 15, 2011

(86) PCT No.: PCT/GB2011/050288
§ 371 (c)(1),
(2), (4) Date: Oct. 27, 2012

(87) PCT Pub. No.: WO2011/101665
PCT Pub. Date: Aug. 25, 2011

(65) Prior Publication Data
US 2013/0109877 A1    May 2, 2013

Related U.S. Application Data

(60) Provisional application No. 61/305,002, filed on Feb. 16, 2010.

(51) Int. Cl.
*C07F 15/00* (2006.01)
*C01B 9/00* (2006.01)

(52) U.S. Cl.
USPC .......................................... 556/136; 423/463

(58) Field of Classification Search
USPC .......................................... 556/136; 423/463
See application file for complete search history.

(56) References Cited

U.S. PATENT DOCUMENTS

2010/0167408 A1    7/2010    Walter et al.

OTHER PUBLICATIONS

Zhao et al., "Syntheses and structural characterization of novel heteroannular cyclopalladated ferrocenylimine,"*Journal of Organometallic Chemistry*, vol. 691, No. 1-2, Jan. 1, 2006, pp. 255-260.
Milani et al., "Bis-Chelated Palladium(II) Complexes with Nitrogen-Donor Chelating Ligands Are Efficient Catalyst Precursors for the CO/Styrene Copolymerization Reaction," *Organometallics*, vol. 16, No. 23, Nov. 1997, pp. 5064-5075.
Ukai et al., "Chemistry of dibenzylideneacetone-palladium(0) complexes: I. Novel tris(dibenzylideneacetone)dipalladium(solvent) complexes and their reactions with quinones," *Journal of Organometallic Chemistry*, vol. 65, No. 2, Jan. 29, 1974, pp. 253-266.
López et al., "Synthesis and structural study of neutral mononuclear and anionic binuclear 2,4,6-trifluorophenyl derivatives of palladium(II). Crystal structure of $[P(CH_2Ph)Ph_3]_2[(C_6F_3H_2)_2Pd(\mu\text{-}SCN)(\mu\text{-}NCS)Pd(C_6F_3H_2)_2]$," *Journal of the Chemical Society, Dalton Transactions*, No. 5, 1990, pp. 1621-1626.
International Search Report dated Jul. 8, 2011, from PCT International Application No. PCT/GB2011/050288.

*Primary Examiner* — Porfirio Nazario Gonzalez
(74) *Attorney, Agent, or Firm* — Young & Thompson

(57) ABSTRACT

The present invention provides a process for the preparation of $Pd_2(dba)_3 \cdot CHCl_3$ comprising the steps of: (a) reacting a Pd(II) complex with an alkali metal halide in at least one alcohol solvent; and (b) reacting the product of step (a) with a mixture comprising dibenzylideneacetone, chloroform and an inorganic base to form $Pd_2(dba)_3 \cdot CHCl_3$.

14 Claims, No Drawings

PROCESS FOR THE PREPARATION OF A PALLADIUM COMPLEX

CROSS-REFERENCE TO RELATED APPLICATIONS

This application is the U.S. National Phase application of PCT International Application No. PCT/GB2011/050288, filed Feb. 15, 2011, and claims priority of U.S. Patent Application No. 61/305,002, filed Feb. 16, 2010, the disclosures of all of which are incorporated herein by reference in their entirety for all purposes.

FIELD OF INVENTION

The present invention concerns the preparation of a metal complex, in particular a precious metal $\alpha,\beta$-unsaturated ketonate.

BACKGROUND OF THE INVENTION

Precious metal $\alpha,\beta$-unsaturated ketonates such as tris(dibenzylideneacetone)dipalladium (chloroform) (i.e. $Pd_2dba_3 \cdot CHCl_3$) are used in many chemical processes as catalysts or as components of catalyst systems. Tris(dibenzylideneacetone)dipalladium (chloroform) is typically manufactured from palladium (II) chloride. For example, Ukai et al, J. Organomet. Chem., 65 (1974), 253-266 describes a two step process where the initially isolated $Pd(dba)_2$ is recrystallised in a mixture of chloroform and ether solvents. It has been found that this method has several limitations when increasing the scale of the reaction. Firstly, since $Pd(dba)_2$ is not very soluble in chloroform, large amounts of chloroform are needed. Secondly, in order to minimise the exposure time of the $Pd(dba)_2$ to the hot chloroform, the $Pd(dba)_2$ is usually added to gently boiling chloroform and filtered. While this step is possible on a laboratory scale, it becomes an escalating problem when the scale of the reaction is increased. Thirdly, a large amount of diethyl ether is required to precipitate/crystallise the product.

SUMMARY OF THE INVENTION

It is an object of the present invention to provide an alternative process for the preparation of tris(dibenzylideneacetone)dipalladium (chloroform). The process is convenient, economic, efficient and may be carried out on a large scale. In some embodiments, nearly quantitative yields of $Pd_2dba_3 \cdot CHCl_3$ can be obtained.

In one aspect, the invention provides a process for the preparation of $Pd_2(dba)_3 \cdot CHCl_3$ comprising the steps of:
(a) reacting a Pd(II) complex with an alkali metal halide in at least one alcohol solvent; and
(b) reacting the product of step (a) with a mixture comprising dibenzylideneacetone, chloroform and an inorganic base to form $Pd_2(dba)_3 \cdot CHCl_3$.

In another aspect, the invention provides a process for the preparation of $Pd_2(dba)_3 \cdot CHCl_3$ comprising the step of reacting $M_2Pd(Hal)_4$ with a mixture comprising dibenzylideneacetone, chloroform and an inorganic base to form $Pd_2(dba)_3 \cdot CHCl_3$, wherein M is an alkali metal cation and Hal is a halide.

In another aspect, the invention provides a process for the preparation of $M_2Pd(Hal)_4$, wherein M is an alkali metal cation and Hal is a halide, comprising the step of reacting a Pd(II) complex such as $Pd(Hal)_2$, $Pd(diolefin)(Hal)_2$ or $Pd(CH_3CN)(Hal)_2$ with an alkali metal halide in at least one alcohol solvent.

DETAILED DESCRIPTION OF THE INVENTION

As mentioned, one aspect of the present invention is to provide a process for the preparation of $Pd_2(dba)_3 \cdot CHCl_3$ comprising the steps of:
(a) reacting a Pd(II) complex with an alkali metal halide salt in at least one alcohol solvent; and
(b) reacting the product of step (a) with a mixture comprising dibenzylideneacetone, chloroform and an inorganic base to form $Pd_2(dba)_3 \cdot CHCl_3$.

The Pd(II) complex is preferably selected from the group consisting of $Pd(Hal)_2$, $Pd(diolefin)(Hal)_2$ and $Pd(CH_3CN)(Hal)_2$.

The halide may be chloride, bromide or iodide, preferably chloride or bromide and more preferably chloride. As used herein, "halide" and "Hal" may be used interchangeably.

Preferably, the diolefin contains a cyclic diolefin, more preferably 2,5-norbornadiene (NBD) or 1,5-cyclooctadiene (COD). Alternatively the cyclic diolefin can be replaced by either two molecules of an olefin such as ethylene or two molecules of a $C_{5-10}$ cycloalkene.

Suitable Pd(II) complexes include $PdCl_2$, $PdBr_2$, $Pd(COD)Cl_2$, $Pd(COD)Br_2$, $Pd(NBD)Cl_2$, $Pd(NBD)Br_2$, $Pd(CH_3CN)_2Cl_2$, $Pd(CH_3CN)_2Br_2$. $PdCl_2$ is a particularly preferred Pd(II) complex.

The alkali metal halide is preferably selected from the group consisting of lithium halide, sodium halide, potassium halide and a combination thereof. Suitable alkali metal halides include lithium chloride, sodium chloride, potassium chloride, lithium bromide, sodium bromide, potassium bromide. Lithium chloride is a particularly preferred alkali metal halide. In one embodiment, the alkali metal halide is anhydrous.

The Pd(II) complex and alkali metal halide are reacted in at least one alcohol solvent. By "alcohol solvent" we mean a liquid alcohol that is able to dissolve the Pd(II) complex to form solutions that are preferably in the range of 0.01-1 molar. Suitable alcohol solvents have boiling points at atmospheric pressure (i.e. $1.0135 \times 10^5$ Pa) below about 180° C., more preferably below about 160° C. and even more preferably below about 120° C. Preferred examples are methanol, ethanol, propanol isomers (i.e. n-propanol or i-propanol), butanol isomers (i.e. 1-butanol, 2-butanol or 2-methyl-2-propanol), pentanol isomers (e.g. 1-pentanol, 2-pentanol, 3-pentanol, 2-methyl-2-butanol, cyclopentanol), hexanol isomers (e.g. 1-hexanol or cyclohexanol). A particularly preferred alcohol solvent is ethanol.

In combining the Pd(II) complex and the alkali metal halide in the at least one alcohol solvent, the components may be mixed in any order, although preferably the Pd(II) complex is first dissolved in the at least one alcohol and then the alkali metal halide is added.

After the reaction of the Pd(II) complex with the alkali metal halide preferably the mixture is stirred at a temperature in the range from about 20° C. to about 50° C., more preferably from about 20° C. to about 30° C. and especially at about room temperature (i.e. about 25° C.). The mixture may be stirred for a period e.g. preferably 1 minute to 24 hours. When the Pd(II) complex is selected from the group consisting of $Pd(Hal)_2$, $Pd(diolefin)(Hal)_2$ and $Pd(CH_3CN)(Hal)_2$, a $M_2Pd(Hal)_4$ complex (where M is an alkali metal cation) in an alcohol solvent is formed.

If desired, the product of step (a) in the at least one alcohol solvent may be used directly in step (b). In this case, it may be desirable to first partially concentrate a solution of the complex in the at least one alcohol solvent (for example, by distillation or stripping methods) and/or filter the solution to remove any insoluble materials present.

However, it may be desirable to recover the product of step (a) prior to step (b), in which case the product of step (a) may be separated from the reaction mixture by any appropriate method which is dependent upon the physical form of the product.

The product of step (a) is reacted with a mixture comprising dibenzylideneacetone, chloroform and an inorganic base to form $Pd_2(dba)_3 \cdot CHCl_3$.

The dibenzylideneacetone ligand may be used in the process of the invention as obtained from the manufacturer or may be purified beforehand (for example, by recrystallisation). Preferably, the dibenzylideneacetone is present in stoichiometric excess. Preferably, the molar ratio of Pd(II) complex:dibenzylideneacetone is about 2:3.05 to about 2:3.25 and more preferably about 2:3.20.

The chloroform is present in situ during the formation of the $Pd_2(dba)_3$ complex and may act as a solvent, as well as a reagent. Any suitable quantity therefore of chloroform may be used.

The inorganic base may be a weak inorganic base such as an alkali metal acetate. Suitable examples of alkali metal acetates include lithium acetate, sodium acetate and potassium acetate. Sodium acetate is a particularly preferred inorganic base.

In a preferred embodiment, the mixture comprising dibenzylideneacetone, chloroform and the inorganic base may further comprise at least one alcohol. Suitable alcohols will generally be similar to those previously mentioned above in connection with step (a). In one embodiment, the alcohol is ethanol.

In one embodiment of the invention, the product of step (a) is added in one portion to the mixture comprising dibenzylideneacetone, chloroform and an inorganic base. In a particularly preferred embodiment of the invention, however, the product of step (a) is added to the mixture comprising dibenzylideneacetone, chloroform and an inorganic base over a period of time of up to about 60 minutes and more preferably up to about 30 minutes.

The reaction of step (b) is preferably carried out at one or more temperatures between about 49° C. to about 53° C. While the reaction temperature may be lower than about 49° C., it has been found that the dibenzylideneacetone does not dissolve fully into solution with the result that the reaction to form the desired $Pd_2(dba)_3 \cdot CHCl_3$ complex may not go to completion. When the reaction temperature is above about 53° C., the $Pd_2(dba)_3 \cdot CHCl_3$ complex may undergo reduction to yield palladium metal. While the temperature range has been given as between about 49° C. to about 53° C., slight variations (e.g. 0.5° C.) below about 49° C. and above about 53° C. may be acceptable without adversely affecting the reaction.

When the product of step (a) is added over a period of time, it is desirable to maintain the reaction temperature between about 49° C. to about 53° C. Without wishing to be bound by theory, it is believed that this prevents the dibenzylideneacetone precipitating out of the reaction mixture due to the drop in the reaction mixture temperature when the product of step (a) is added. As the dibenzylideneacetone would not redissolve quickly, the stoichiometry of the reaction would be adversely effected, even if the reaction temperature was returned to a temperature between about 49° C. to about 53° C.

In an alternative embodiment, the product of step (a) may be added to the mixture comprising the dibenzylideneacetone, chloroform and inorganic base and the reaction heated to between about 49° C. and about 53° C.

The mixture may be stirred or agitated for a period e.g. preferably 1 minute to 3 hours, more preferably 2 minutes to 1.5 hours and most preferably 2.5 minutes to 1 hour.

The reactants may be added in any suitable order, but in a preferred process of the invention the dibenzylideneacetone ligand is placed in a reaction vessel, together with the chloroform, the inorganic base and an alcohol (if used), heated and then the product of step (a) is added.

Step (a) and/or step (b) are preferably carried out under an inert atmosphere, such as under nitrogen or argon. If the product of step (a) is in solution prior to step (b), the solution may be degassed before its reaction with the mixture comprising dibenzylideneacetone, chloroform and the inorganic base.

In one embodiment, the reaction mixture may be cooled to room temperature (i.e. about 25° C.) and the reaction mixture stirred or agitated during this time.

The $Pd_2(dba)_3 \cdot CHCl_3$ complex product may be recovered directly by filtering, decanting or centrifuging. If desired a proportion of the chloroform and any alcohol (if present) may be evaporated prior to recovery of the complex.

Howsoever the complex is recovered, the separated complex is preferably washed one or more times with water and, if desired, alcohol and then dried. The complex may then be combined with further alcohol and chloroform, re-filtered, washed with alcohol and dried. Drying may be performed using known methods, for example at temperatures in the range 10-60° C. and preferably 20-40° C. under 1-30 mbar vacuum for 1 hour to 5 days. If desired the complex may be recrystallised.

The $Pd_2(dba)_3 \cdot CHCl_3$ complex may be prepared on any desired scale. For example, it has been found that the above-mentioned process may be reliably scaled up to prepare over 500 g of $Pd_2(dba)_3 \cdot CHCl_3$.

In another aspect, the present invention provides a process for the preparation of $Pd_2(dba)_3 \cdot CHCl_3$ comprising the step of reacting $M_2Pd(Hal)_4$ with a mixture comprising dibenzylideneacetone, chloroform and an inorganic base to form $Pd_2(dba)_3 \cdot CHCl_3$, wherein M is an alkali metal cation (e.g. $Li^+$, $Na^+$ or $K^+$) and Hal is a halide.

Suitable inorganic bases, as well as reaction and isolation conditions will generally be similar to those previously mentioned above.

The invention will be further described in the following non-limiting Examples.

EXAMPLES

General

Palladium dichloride and anhydrous sodium acetate was obtained from Johnson Matthey. Lithium chloride was obtained from Alfa Aesar. Dibenzylideneacetone (dba) was obtained from Espirit, UK (Wychem Limited). Chloroform (99.9% A.C.S., HPLC grade) was obtained from Aldrich. IR spectra were recorded on a Nicolet 360 FT-IR as a KBr—$Pd_2(dba)_3$-$CHCl_3$ mixture using the reflective mode.

Preparation of $Li_2PdCl_4$ Solution

Palladium dichloride (200.2 g), lithium chloride (108 g) and ethanol (5400 ml) were added together under a nitrogen atmosphere and the solution agitated at room temperature overnight. The Li$_2$PdCl$_4$ solution was filtered and the insolubles washed with ethanol (50-100 ml).

Preparation of Pd$_2$(dba)$_3$·CHCl$_3$

Dibenzylideneacetone (414.3 g, 3.20 molar ratio), ethanol (8360 ml), CHCl$_3$ (2250 ml) and sodium acetate (720.4 g) were added together under a nitrogen atmosphere and the solution agitated.

The Li$_2$PdCl$_4$ solution was degassed under nitrogen and added to the dba solution over a period of 30 minutes at a temperature of 50.6-53.2° C. The reaction conditions were maintained for a further hour after the addition of the Li$_2$PdCl$_4$ solution and the temperature maintained at 50.9-52.3° C.

The reaction mixture was cooled to room temperature and the agitation continued during this time. The reaction mixture was filtered, the product filter-washed with deionised water (3000 ml) and vacuum dried under nitrogen for 30 minutes. A blackish purple solid was obtained containing some visible white sodium acetate. The solid was combined with deionised water (11000 ml). The solution was agitated for 15 minutes under nitrogen and filtered. The blackish purple solid was filter-washed with deionised water (1500 ml) and ethanol (1500 ml). The solid was vacuum dried for 30 minutes under nitrogen.

The solid was combined with ethanol (1800 ml) and CHCl$_3$ (900 ml) and the solution stirred. The reaction mixture was filtered and filter-washed with ethanol (50 ml). The solid was vacuum dried for one hour under nitrogen. The product was placed in a glass tray and dried under vacuum for 16 hours at 25-35° C. and a pressure of −15 inches Hg to constant weight to obtain the title product (97.76%; melting point 125-130° C.).

The invention claimed is:

1. A process for the preparation of Pd2(dba)$_3$·CHCl$_3$ comprising the steps of:
   (a) reacting a Pd(II) complex with an alkali metal halide in at least one alcohol solvent; and
   (b) reacting the product of step (a) with a mixture comprising dibenzylideneacetone, chloroform and an inorganic base to form Pd2(dba)$_3$·CHCl$_3$.

2. The process according to claim 1, wherein the Pd(II) complex is selected from the group consisting of Pd(Hal)$_2$, Pd(diolefin)(Hal)$_2$ and Pd(CH$_3$CN)(Hal)$_2$.

3. The process according to claim 1, wherein the alkali metal halide is selected from the group consisting of lithium halide, sodium halide, potassium halide and a combination thereof.

4. The process according to claim 3, wherein the alkali metal halide is lithium chloride.

5. The process according to claim 1, wherein the at least one alcohol solvent has a boiling point below 180° C. at atmospheric pressure.

6. The process according to claim 1, wherein step (a) is carried out at a temperature from about 20° C. to about 50° C.

7. The process according to claim 1, wherein the product of step (a) is recovered prior to step (b) or the product of step (a) is used directly in step (b).

8. The process according to claim 1, wherein the molar ratio of Pd(II) complex:dibenzylideneacetone is about 2:3.05 to about 2:3.25.

9. The process according to claim 8, wherein the molar ratio of Pd(II) complex:dibenzylideneacetone is about 2:3.20.

10. The process according to claim 1, wherein the inorganic base is an alkali metal acetate.

11. The process according to claim 1, wherein the product of step (a) is added to the mixture comprising dibenzylideneacetone, chloroform and an inorganic base over a period of time of up to about 60 minutes.

12. The process according claim 1, wherein step (b) is carried out at one or more temperatures between about 49° C. to about 53° C.

13. The process according to claim 1, wherein the mixture comprising dibenzylideneacetone, chloroform and an inorganic base further comprises at least one alcohol.

14. A process for the preparation of Pd$_2$(dba)$_3$·CHCl$_3$ comprising the step of reacting M2Pd(Hal)$_4$ with a mixture comprising dibenzylideneacetone, chloroform and an inorganic base to form Pd$_2$(dba)$_3$·CHCl$_3$, wherein M is an alkali metal cation and Hal is a halide.

* * * * *